United States Patent [19]

Morrison

[11] 3,975,641

[45] Aug. 17, 1976

[54] LOW LEVEL SNOW PRECIPITATION GAUGE

[75] Inventor: Roderick G. Morrison, Boise, Idaho

[73] Assignee: Idaho Industrial Instruments, Inc. (Entire), Boise, Idaho

[22] Filed: Aug. 23, 1974

[21] Appl. No.: 500,174

[52] U.S. Cl. ............................ 250/393; 250/357
[51] Int. Cl.² ........................................... G01T 1/00
[58] Field of Search ............ 250/358, 357, 388, 393, 250/395

[56] References Cited
UNITED STATES PATENTS

| | | | |
|---|---|---|---|
| 3,665,180 | 5/1972 | Guillot et al. | 250/388 |
| 3,843,887 | 10/1974 | Morrison | 250/358 |

*Primary Examiner*—Davis L. Willis
*Attorney, Agent or Firm*—Clarance A. O'Brien & Harvey B. Jacobson

[57] ABSTRACT

A solid, annular body embedding naturally occurring radioisotopes, forms a source of radiation bordering the opening of a basin at ground level, into which water percolates from a body of precipitation in the form of snow and ice accumulated on a porous cover closing the opening. Point detectors above the opening and below the basin sense radiation emitted from the source to produce signals attenuated by the accumulated precipitation reflecting changes in density thereof. Other detectors laterally spaced from the source of radiation both inside and outside its signal range, respectively measure changes in soil density and background radiation.

22 Claims, 4 Drawing Figures

LOW LEVEL SNOW PRECIPITATION GAUGE

This invention relates to the accurate gauging of precipitation accumulated at a given location over a prolonged period of time and provides a continuous measure of above ground water inventory.

The present invention is related to my prior copending U.S. application, Ser. No. 229,266, entitled "Self Calibrating Isotopic Precipitation Measurement Gauge", filed Feb. 25, 1972, now U.S. Pat. No. 3,843,887, and utilizes techniques similar to those in said prior application wherein measurements for very deep snow fields are involved utilizing artificial radioisotopes. Most of the presipitation on earth is, however, measured at locations where less than two meters of snow accumulate. Non-licensable quantities of natural radioactive materials are therefore utilized in this invention to measure such accumulations by the proper arrangement of the radioactive source of materials based on the average gamma energies emitted.

For timely predictions of flood conditions, river runoff, and reservoir management, accurate and reliable systems are required for remote and unattended installations. Such systems must consume low power, be adaptable to land line or radio telemetry. Since a snow field loses a significant part of its water inventory in the form of evaporation, it is extremely important to monitor the actual water inventory at periodic intervals to account for this loss.

Precipitation gauges in use are generally in the form of a catch basin from which a measurement of the change in weight of the basin infers the total precipitation deposited. These systems provide accurate data provided the catch basin has an opening representative of average precipitation falling downward over a given area and provided the collected precipitation is held in liquid form. The entrapment of snow in the catch basin is, however, difficult since snow seldom falls vertically, but rather at changing angles of descent. To establish a representative sample for these gauges, fluttering devices called wind deflectors, are installed around the intake of the catch basin to direct entry of the snow in a vertical descent and antifreeze solutions or heating devices are installed to assure that the snow is transformed into liquid and is in suitable form for weighing. The weight of the tank is generally measured by strain gauges, force gauges, or pressure sensors which are complex and need careful temperature compensation. A major problem also experienced with such weighing devices, is the establishment of an accurate sample of precipitation from an area large enough to be representative of the average precipitation in a given locale. Other weighing devices, such as tipping buckets, which depend on precipitation in the form of water, and snow pillows which measure the pressure of a snow pack, measure only a single parameter, the weight of the liquid precipitation or snow structural pressure.

Prior U.S. patents known to applicant, and relating to measurements made by use of radiation and logic circuit techniques, are as follows: U.S. Pat. Nos. 3,098,154, 3,389,250, 3,486,025, 3,489,901, 3,657,532 and 3,676,649.

It is, therefore a principal object of this invention to provide measurements heretofore made by precipitation gauges, utilizing natural radioactive materials without any physical hazard to biological systems and requiring no Federal or State license for use.

It is a further object of this invention to gauge precipitation with a simple system embodying no moving parts, with minimum disturbance of the natural surroundings and to provide a real measurement based on several parameters over a representative area.

To accomplish the foregoing objectives, a mixture of naturally occurring aggregate and radioactive substances, such as uranium or thorium bearing ores and ordinary binders, such as asphalt or cement, are utilized. The mixture is formed into a preferred, geometrical configuration, such as a ring, with sufficient isotopic inventory to create an isoflux line at a detector of approximately 15 times the natural background radiation. The radioactive, ring-shaped source serves as a transmitter of electromagnetic signals emitted from a geometrically fixed zone to a point detector at a fixed location. The ring source and point detector thus forms a convergent isoflux at the detector providing a $2\pi$ count at the detector as opposed to a unit count from a point source and a point detector. The measurement of the attenuation of the transmitted signals then establishes the density of the substances accumulated between the source and the detector. Any change in this attenuation can thus be correlated to water which is a measure of precipitation.

These together with other objects and advantages which will become subsequently apparent reside in the details of construction and operation as more fully hereinafter described and claimed, reference being had to the accompanying drawings forming a part hereof, wherein like numerals refer to like parts throughout.

Figure 1:
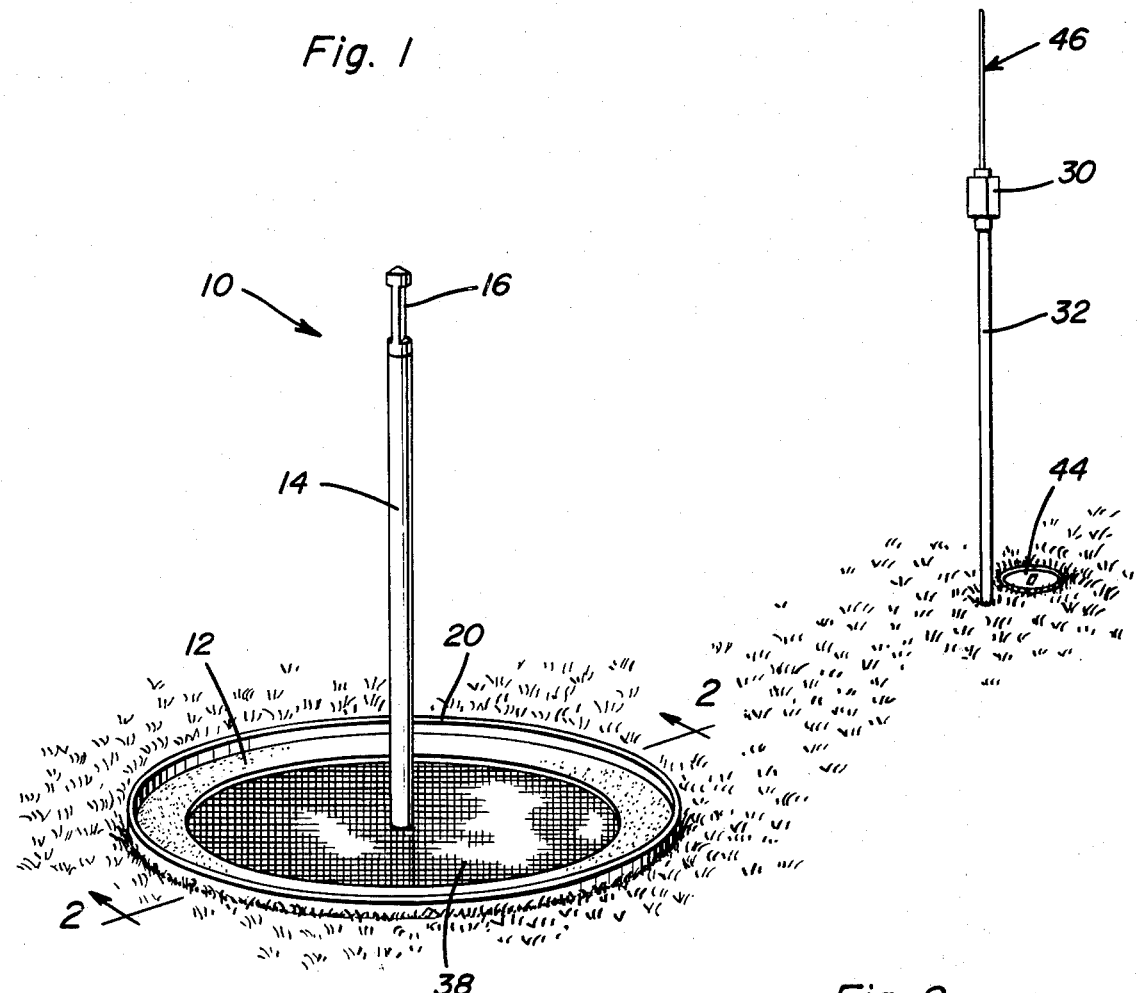
FIG. 1 is a prespective view showing a typical installation of the present invention.
Figure 3:
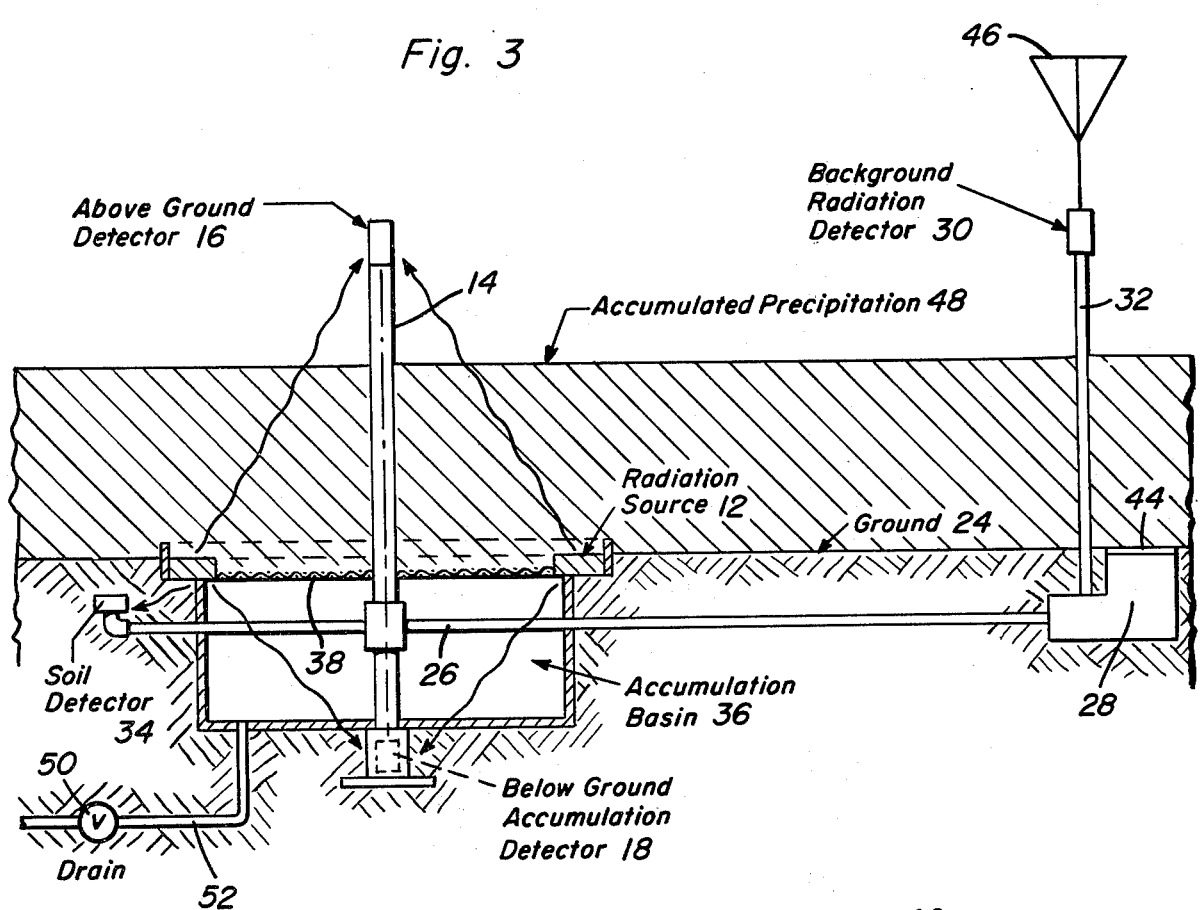
FIG. 3 is a schematic side sectional view of the installed apparatus of the present invention.

Referring now to the drawings in detail, in the embodiment illustrated in FIGS. 1 and 3, the gauge system generally denoted by reference numeral 10 consists of a source 12 of spatially distributed radioactive signals in the form of concrete blocks containing naturally occurring radioactive ore and arranged in an annular or ring-shaped configuration approximately two meters in diameter. The most attractive natural radioisotopes for the source 12 are found in the thorium ($4n$) and uranium ($4n+2$) series of ores. These ores contain the basic isotope along with daughter products which have reached secular equilibrium, thus creating these daughter products at the same rate as they are decaying. The extremely long half-life of the material (greater than $10^9$ years) produces a stable source of radiation for which no decay corrections need be made. With the spectrum of gamma energies available, an attenuation measurement is easily achieved. Naturally found ores, such as euxenite, are most adaptable since they are insoluble to water and have a usable escape spectrum of gamma energies from 0.1 Mev to approximately 2.0 Mev. This characteristic establishes the practical limit of approximately two meters of snow depth and a snow water equivalent of averge density of approximately 35 grams per cubic centimeter.

Figure 2:
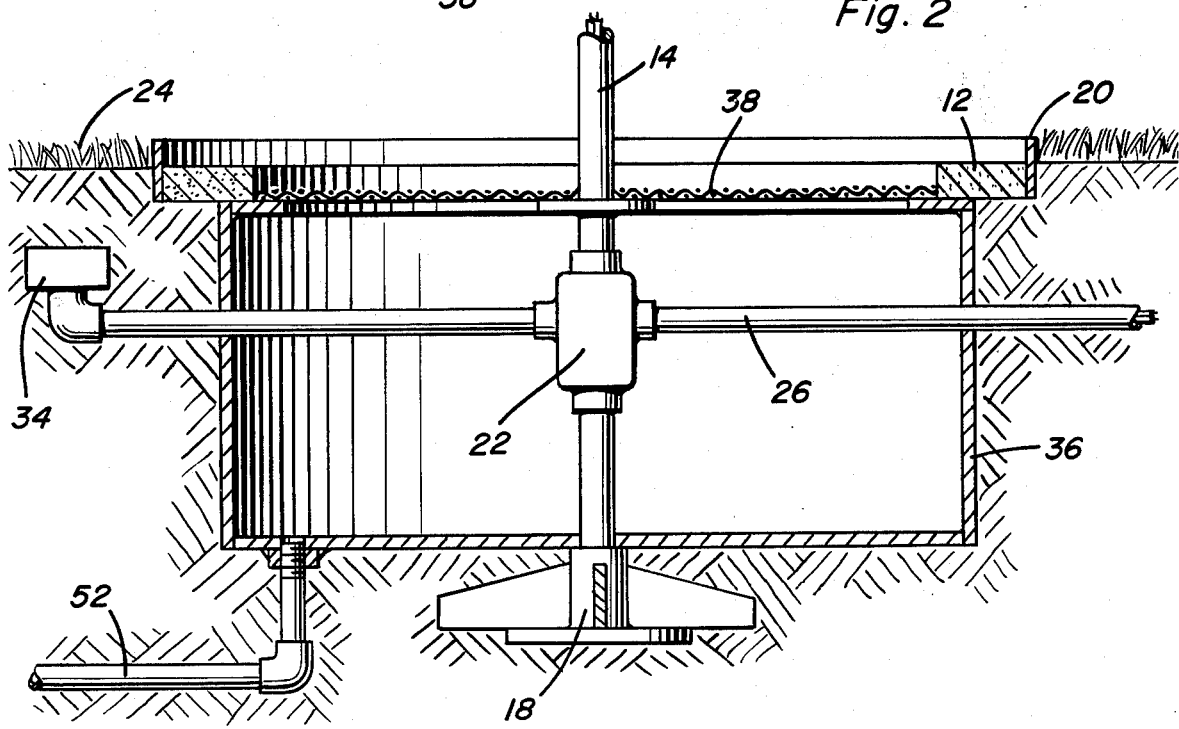
FIG. 2 is a side sectional view taken substantially through a plane indicated by section line 2—2 of FIG. 1.

A single vertical pipe or pole 14 having an upper end approximately two meters above ground surface, is centrally mounted within the annular configuration of source 12 and supports on top thereof a radiation detector 16. Another radiation detector 18 is mounted at the lower end of the pipe 14 approximately 75 centimeters below the ground surface at which the pipe is anchored as shown in FIG. 2. The distance from the ring source 12 and the detectors 16 and 18 are thus fixed by the pipe 14 to establish above ground and below surface radiation signal paths, as shown in FIG. 3. A protective rim 20 encircles the sources 12 and projects above the ground.

Electronic signal cables extend through the pipe 14 to a pipe coupling 22 embedded a short distance below ground level 24. A conduit 26 extends horizontally through the coupling 22 to an enclosure 28 remotely spaced from the source 12, outside of its signal range as diagramatically shown in FIG. 3. A third radiation detector 30 is placed on a vertical transmitter pole 32 at a distance above ground surface approximately the height of the radiation detector 16. At a shorter distance, laterally spaced from the source 12 within its signal range, a fourth detector 34 is positioned below the ground level as shown in FIGS. 2 and 3 within the usable radiation field or signal range of the source 12. A catchment basin or tank 36 is placed below the source 12 and above the detector 18. This basin has an opening exposed within the ring source 12 but covered by a porous lid 38 through which the pipe 14 extends. The conduit 26 extends through the basin 36 between the soil detector 34 and the enclosure 28 from which the transmitter pole 32 extends upwardly.

The upper radiation detector 16 on the pipe 14 is used to measure the precipitation above ground. The lower radiation detector 18 is used to measure the precipitation entrapped in the basin 36. Signals emitted from the source 12 and received by the radiation detectors 16 and 18, are routed via signal cables in the pipe 14 and conduit 26 to an electronic counting network 40 located within the enclosure 28. The measurements of the counting network are recorded by a recorder 42 also located within the enclosure 28, for a specific duty cycle determined by the updating and measurement accuracy requirements of the gauge installation. The below ground soil detector 34 is used to measure the changes in soil moisture content as a function of precipitation precolating into the ground. The signals received by this detector are also routed to the counting network 40 by signal cables in conduit 26. The radiation detector 30 on the transmitter pole 32, is used to measure variations in natural background radiation in order to establish a correlation factor for the other three radiation detectors. The signals received by the detector 30 are routed by signal cables in transmitter pole 32 to the electronic counting network 40. Access to the recorder 42 in the enclosure 28 is provided by a removable cover plate 44 on the enclosure which is exposed at the ground surface adjacent the transmitter pole 32, as shown in FIGS. 2 and 3. Data from the network 40 that is recorded by the recorder 42 is also transmitted to a remote location by modulation of a radio transmitter in the enclosure 28 to which an antenna assembly 46 is connected, the antenna assembly being mounted atop the pole 32.

As precipitation accumulates in the form of snow or sleet 48, as diagrammed in FIG. 3, fewer electromagnetic signals will reach the detector 16 from source 12. The number of counts received by detector 16 is correlated to the average amount of precipitation above the source 12. As the snow or sleet changes to water and percolates into the basin 36, a reduction in electromagnetic signals received by detector 18 occurs. The signal count of detector 18 is correlated to the amount of water percolating through to the ground and entrapped in basin 36. While the snow pack exists, precipitation in the form of sleet, snow or rain will be monitored above the ground surface. At the onset of a melt cycle, the water evaporated can be measured by the total above ground water equivalent by correlating the above ground measurement to the below ground measurement of detector 18 representing the water available for run-off or ground absorption.

The precipitation entrapped in basin 36 is periodically released at the end of the season by means of a valve 50 in drain line 52, as diagrammed in FIG. 3. The dimensions of the basin 36 are determined by the average expected precipitation in a given period of time, the duty cycle required by the measurement system, and the penetration characteristics of the electromagnetic signals emanating from the source 12, and the opening closed by the porous lid 38. The depth of the basin 36 is established by the gamma penetration characteristics, the radioactive material of the source and the width of the basin as determined from the total area of the opening covered by lid 38.

The detectors used for the present invention are conventional "GM" tubes with appropriate wall thicknesses to afford energy discriminations over prolonged counting times and to reduce the effects of scattered radiations from the snow pack. Since the counting times are extremely long, this enables statistical discrimination to record mainly those gamma energies which originate from the source, thus establishing a direct attenuation measurement of density.

Figure 4:
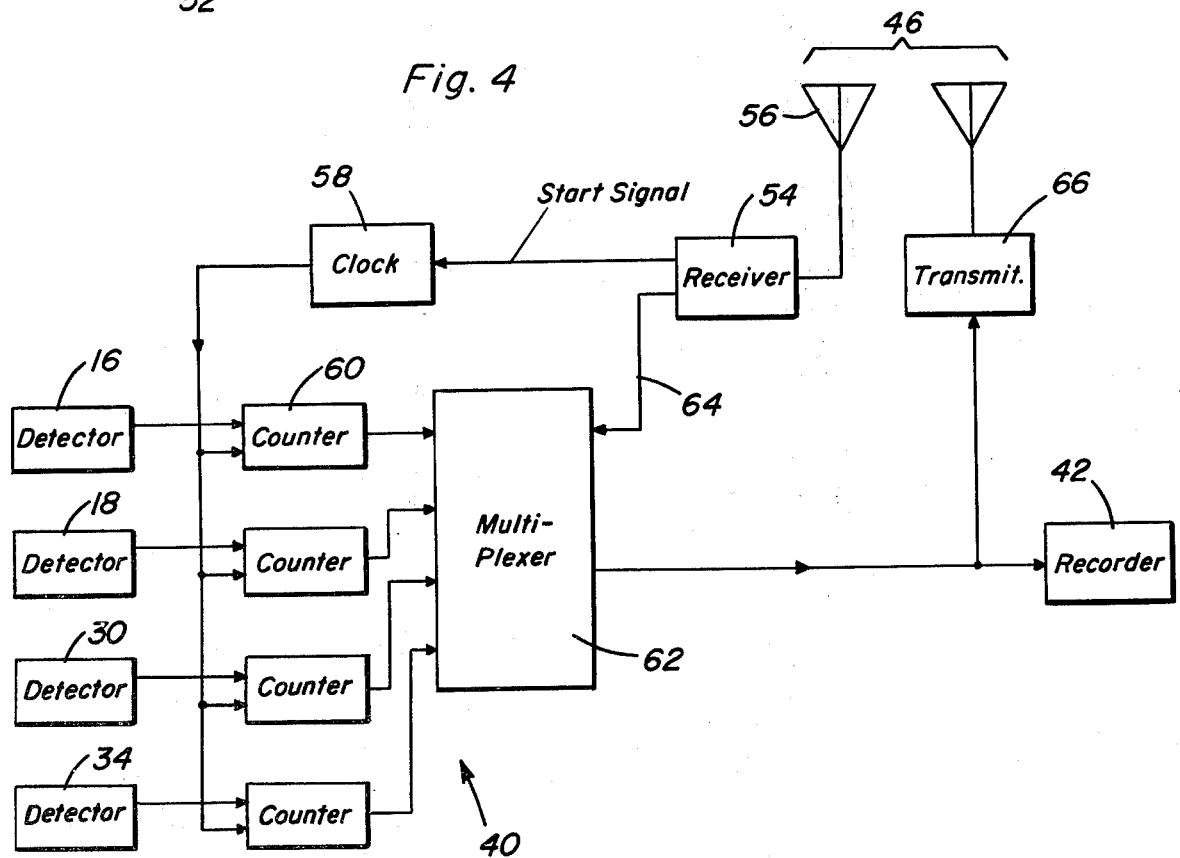
FIG. 4 is a functional block diagram of the electronic signal monitoring system associated with the present invention.

FIG. 4 represent a simplified diagram of the electronic counting network 40. Since solid state electronics are well understood by those skilled in the art, no detailed description of the electronic circuitry and techniques are given herein. For this particular invention, however, high reliability, low temperature components with emphasis on low power consumption are employed. A receiver 54 within enclosure 28 receives data commands through antenna section 56. Each data command starts a clock 58 which simultaneously opens four counting gates associated with counters 60 to which the above ground water equivalent detector 16, the below ground water detector 18, the soil moisture detector 34 and the natural background radiation detector 30 are connected. The outputs of the detectors are thus fed to the gate control counters 60 and after some preselected time, such as one hour, the clock terminates the input to the counters. The data is held in a multiplexer 62 until a readout command is received by receiver 54 and applied through line 64 to the multiplexer 62. This readout command also activates the transmitter 66 and recorder 42 to receive the data. The entire station is designed to operate on rechargeable batteries.

In summary, the precipitation gauge hereinbefore described utilizes a source 12 of naturally occurring radioisotopes arranged in an annular configuration surrounding a vertical pole 14 centrally positioned within the radiation source and instrumented with two radiation detectors 16 and 18 for measuring above and below ground precipitation. A third radiation detector 34 positioned in the soil measures changes in soil moisture content while a fourth radiation detector 30 placed a distance away from the source field, monitors changes in natural background radiation for absolute correction of the readings obtained from the other detectors. The detectors are instrumented with nuclear counting equipment 40 to compare the amount of precipitation above ground in the form of snow or ice or water moving through the snow pack 48, or the total amount of precipitation available for ground water percolation or run-off, and the free water moving through the surface soil. The correlation of the foregoing measured parameters, thus establishes the absolute amount of total precipitation falling over a given area.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A precipitation gauge comprising a source of radiation emitted from a geometrically fixed zone of substantial extent, a plurality of detectors, means mounting said detectors in fixed spaced relation to each other for receiving said radiation from said source at point locations spaced from said geometrically fixed zone and means connected to said detectors for registering changes in radition density as a result of radiation attenuation along radiation paths between said fixed zone and said point locations.

2. The combination of claim 1 wherein said fixed zone is an annular configuration positioned substantially at ground level.

3. The combination of claim 2 wherein said source is formed from naturally occurring radioisotopes deposited within a solid binder.

4. The combination of claim 3 wherein said mounting means for said detectors includes a vertical pole extending above and below ground level and supporting two of said detectors above ground and below ground level, respectively, to establish some of said paths above ground and some of said paths below ground level.

5. The combination of claim 4 including a collection basin mounted in underlying relation to said source having an opening bordered by said fixed zone, said below ground level paths extending through said basin, whereby said radiation is attenuated by liquid collected within said basin.

6. The combination of claim 5 including porous means closing said opening in said basin for enabling accumulation of precipitation above ground level over said basin through which said above ground paths extend.

7. The combination of claim 6 wherein said two of said detectors are respectively supported 2 meters above ground level and one-half meter below ground level underlying said basin.

8. The combination of claim 7 including a third of said detectors supported by said mounting means in laterally spaced relation to said source below ground level establishing a subsoil radiation path within an effective radiation range of said source to measure changes in soil density.

9. The combination of claim 8 including a background radiation detector mounted above ground level remotely spaced from said source outside of said effective signal range thereof, and means connecting said background radiation detector to said registering means for correcting measurements of changes in densities of accumulated precipitation and collected liquid in said soil sensed by said third of said detectors.

10. The combination of claim 2 wherein said mounting means for said detectors includes a vertical pole extending above and below ground level and supporting two of said detectors above ground and below ground level, respectively.

11. The combination of claim 10 including a collection basin mounted in underlying relation to said source having an opening bordered by said fixed zone, whereby radiation is attenuated by liquid collected within said basin.

12. The combination of claim 11 including porous means closing said opening in said basin for enabling accumulation of precipitation above ground level over said basin.

13. The combination of claim 12 including a third of said detectors supported by said mounting means in laterally spaced relation to said source below ground level establishing a subsoil radiation path within an effective radiation range of said source to measure changes in soil density.

14. The combination of claim 13 including a background radiation detector mounted above ground level remotely spaced from said source outside of said effective radiation range thereof, and means connecting said background radiation detector to said registering means for correcting measurements of changes in densities of accumulated precipitation and collected liquid in said soil sensed by said third of said detectors.

15. The combination of claim 1 including a collection basin mounted in underlying relation to said source having an opening bordered by said fixed zone, whereby said radiation is attenuated by liquid collected within said basin.

16. The combination of claim 15 including porous means closing said opening in said basin for enabling said accumulation of precipitation above ground level over said basin.

17. The combination of claim 1 wherein said mounting means for said detectors includes a vertical pole extending above and below ground level and supporting two of said detectors above ground and below ground level, respectively.

18. The combination of claim 17 including a collection basin mounted in underlying relation to said source having an opening bordered by said fixed zone whereby said radiation is attenuated by liquid collected within said basin.

19. The combination of claim 18 including a third of said detectors supported by said mounting means in laterally spaced relation to said source below ground level establishing a subsoil radiation path within an effective radiation range of said source to measure changes in soil density.

20. The combination of claim 19 including a background radiation detector mounted above ground level remotely spaced from said source outside of said effective signal range thereof, and means connecting said background radiation detector to said registering means for correcting measurements of changes in densities of accumulated precipitation, and said collected liquid in said soil sensed by said third of said detectors.

21. A precipitation gauge comprising a collection basin having an opening, a source of radiation emitted from a zone bordering said opening, porous means closing said opening for supporting accumulated precipitation above said opening, plural detector means for sensing radiation emitted along paths extending through said accumulated precipitation, through said basin and through soil adjacent to said basin, said plural detector means including detectors along each of the respective paths and radiation counting means connected to said detector means for correlating measured changes in densities of said accumulated precipitation, of said liquid collected in said basin, and the adjacent soil to establish the absolute amount of total precipitation.

22. A precipitation guage comprising a source of electromagnetic radiation emanating from a radioactive substance distributed within a fixed zone of substantial extent, a plurality of detectors producing signals in response to radiation received from said source, means mounting said detectors in spatially fixed positions relative to said fixed zone, and pulse counting means connected to said detectors for registering the number of said signals received as a result of attenuation along paths respectively extending between said source of electromagnetic radiation and said detectors.

* * * * *